United States Patent [19]
Juang

[11] Patent Number: 5,464,017
[45] Date of Patent: Nov. 7, 1995

[54] LED DISPLAY BLOOD PRESSURE METER

[76] Inventor: Jing-Song Juang, No. 236, Fu Teh 2 Rd., Hsichih, Taipei Hsien, Taiwan

[21] Appl. No.: 267,549

[22] Filed: Jun. 29, 1994

[51] Int. Cl.⁶ .................................................. A61B 5/00
[52] U.S. Cl. ......................... 128/672; 128/677; 128/687
[58] Field of Search ................................. 128/672, 677, 128/680–683, 687, 903, 904, 673, 675, 688–690

[56] References Cited

U.S. PATENT DOCUMENTS

| | | | |
|---|---|---|---|
| 4,320,767 | 3/1992 | Villa-Real | 128/680 |
| 4,494,545 | 1/1985 | Slocum et al. | 128/903 |
| 5,054,494 | 10/1991 | Lazzaro et al. | 128/681 |
| 5,193,547 | 3/1993 | Evans, II et al. | 128/673 |

*Primary Examiner*—Lee S. Chen
*Assistant Examiner*—Robert L. Nasser, Jr.
*Attorney, Agent, or Firm*—Bacon & Thomas

[57] ABSTRACT

An LED display blood pressure meter comprising a transmitter, a receiver, a sensor, an amplifying circuit, a transferring circuit, a microprocessor and three display circuits. When measuring human blood pressure, the blood pressure values are sensed and transferred into electronic analog signals by the sensor. The analog signals are amplified by the amplifying circuit and transferred into digital signals by the transferring circuit. The digital signal is then received and processed by the microprocessor which drives the display circuits to display the ascending/descending of the blood pressure values by means of LED array and show the high and low blood pressure values in digital pattern by means of LED displays. The high and low blood pressure values are latched by means of a transmitter and a receiver in remotely controlling manner so as to be stably displayed in a display panel.

4 Claims, 5 Drawing Sheets

LED DISPLAY BLOOD PRESSURE METER

BACKGROUND OF THE INVENTION

The present invention relates to an LED display blood pressure meter.

A conventional blood pressure meter employs mercury column as the blood pressure measuring means in which the high and low blood pressure values are indicated by the scales aligned with the levels of the mercury column. The scales are read directly by the operator and an error will inevitably happen due to the deflection of the sight angle. Moreover, in case such blood pressure meter is damaged or discarded, the mercury is very apt to contaminate the environment.

SUMMARY OF THE INVENTION

It is therefore a primary object of the present invention to provide an LED display blood pressure meter to eliminate the shortcomings existing in the conventional blood pressure meter. In the present blood pressure meter, a pressure sensor senses the blood pressure values and generates signals to be amplified by an amplifying circuit and transferred into digital signals by a transferring circuit. The digital signals are then received and processed by a microprocessor which sends signals to display circuits and drives the same to display the ascending/descending of the blood pressure values by means of LED array and show the high and low blood pressure values in digital pattern by means of LED displays. Because the present invention employs an electronic digitalized displaying manner, the high and low blood pressure values are latched by a transmitter and stably displayed in a display panel so that the reading error is greatly reduced and the problem of environmental pollution caused by the mercury is solved. However, the profile of the present invention is identical to that of the conventional blood pressure meter so that a user can apply the present blood pressure meter in a usual manner without inconvenience.

The present invention can be best understood through the following description and accompanying drawing, wherein:

DETAILED DESCRIPTION OF THE PREFERRED EMBODIMENT

Figure 1:
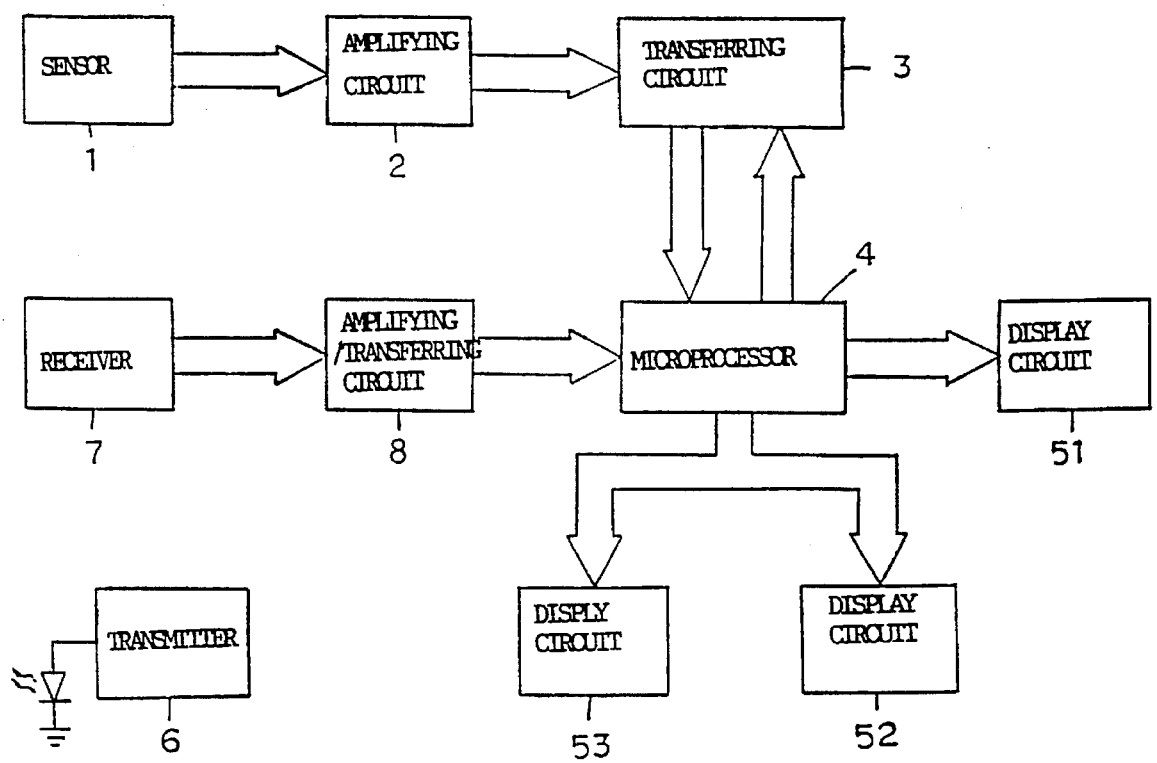
FIG. 1 is a circuit block diagram of the present invention.

Please refer to FIG. 1. The present invention includes a transmitter 6, a receiver 7, a sensor 1, an amplifying circuit 2, a transferring circuit 3, an amplifying/transferring circuit 8, a microprocessor 4 and three display circuits 51, 52 and 53. By means of the expansion of a pressure belt, the sensor 1 generates a sensing signal which is amplified by the succeeding amplifying circuit 2 and then sent to the transferring circuit 3. The pressure signal sensed by the sensor 1 is an analog linear signal which is transferred into a digital signal by the transferring circuit 3. The digital signal is sent to the succeeding microprocessor 4 for comparison. The microprocessor 4 serves as a central processing unit of the present invention, which according to the internally recorded program processes the signal sent from the transferring circuit 3 and sends the signal to the display circuits 51, 52, 53 to display the output data. The display circuit 51 displays the ascending/descending of the blood pressure value on the blood pressure meter which corresponds to the movement of the mercury column of a conventional blood pressure meter. The display circuits 52, 53 display respectively the high blood pressure value and low blood pressure value in such a manner that the transmitter 6 sends out a signal which is received by the receiver 7. The signal is then sent to the microprocessor 4 through the amplifying/transferring circuit 8, informing the microprocessor 4 to latch the high and low blood pressure values and send the same to the display circuits 52, 53 for displaying the values.

Figure 2:
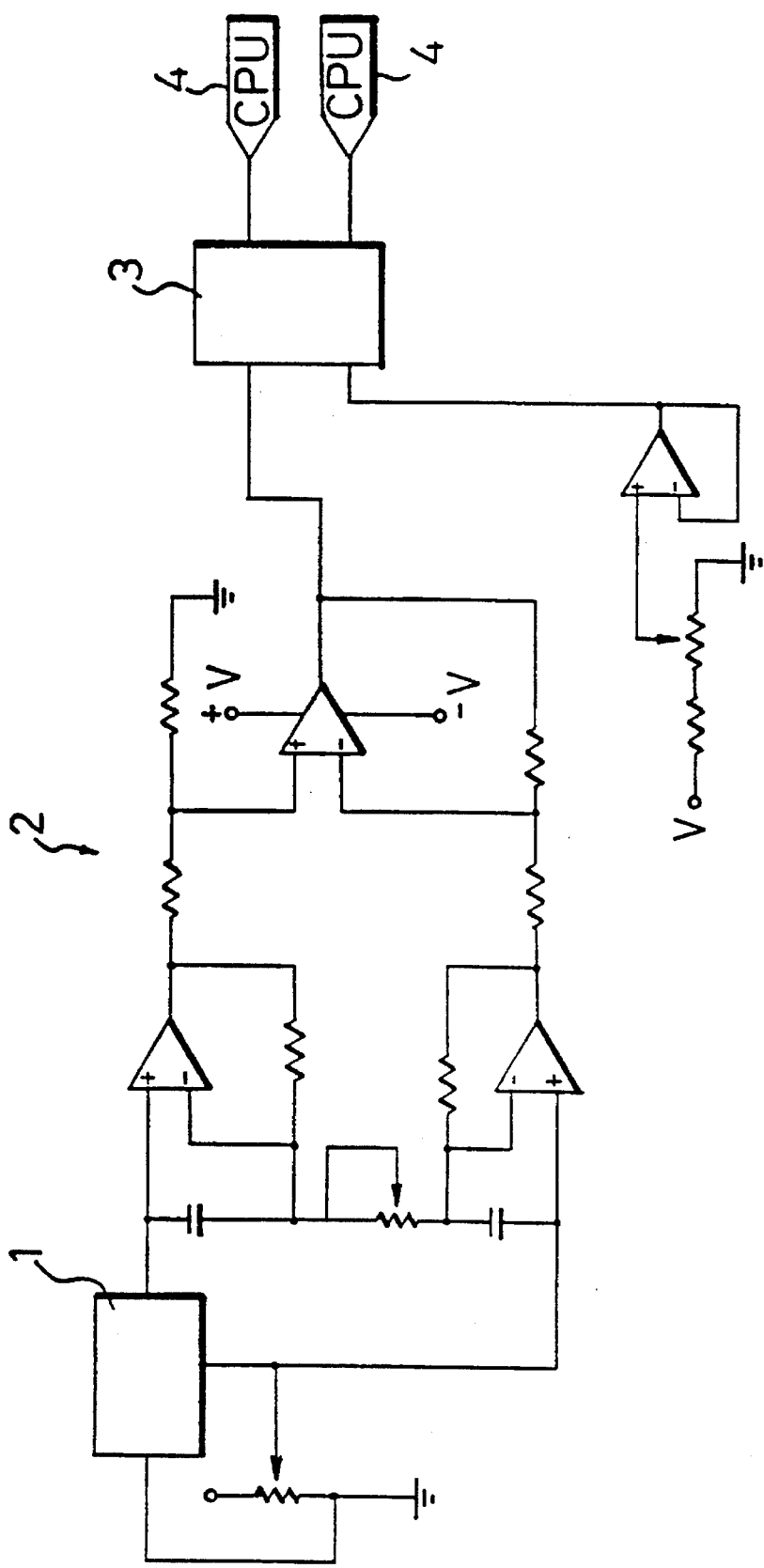
FIG. 2 is a circuit diagram of the sensor and amplifying circuit as well as transferring circuit of the present invention.
Figure 3:
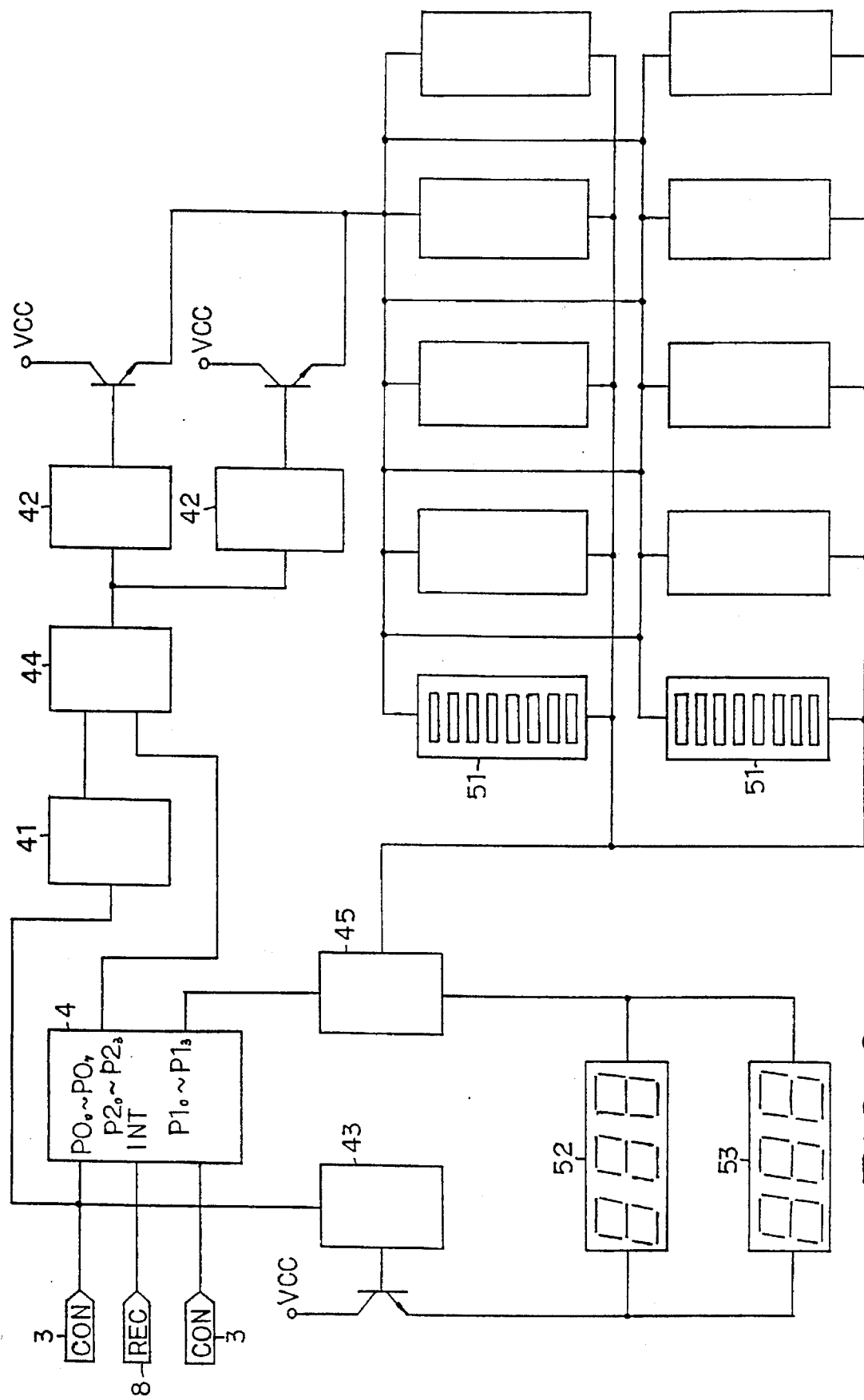
FIG. 3 is a circuit diagram of the microprocessor and display circuits of the present invention.

Please refer to FIG. 2. The signal generated by the sensor 1 due to the pressure change is sent to the succeeding amplifying circuit 2 which is composed of several sets of OPA. This is because the output from the sensor 1 requires an AC amplification of 60–80 dB. The amplified pressure sensing signal is transferred to a digital signal by the transferring circuit 3 which is driven by an IC and outputs several groups of control lines and digitalized pressure signal to the microprocessor 4. Please refer to FIG. 3. The P00–P07 of the microprocessor 4 are connected to the signal output ends of the transferring circuit 3 and the control lines of the transferring circuit 3 are also connected to the several groups of control lines of the microprocessor 4. The microprocessor 4 according to the data sent from the transferring circuit 3 and the internally recorded program respectively drives latching circuits 41, 42, 43, a memory circuit 44 and a decoder circuit 45 via the control lines and output ports P10–P13 and output ports P20–P23 so as to display the pressure values sensed by the sensor 1 by means of the display circuits 51, 52, 53, that is, display the high and low pressure values by means of the LED array of the display circuit 51 and the seven-section displays of the display circuits 52, 53.

Figure 4:
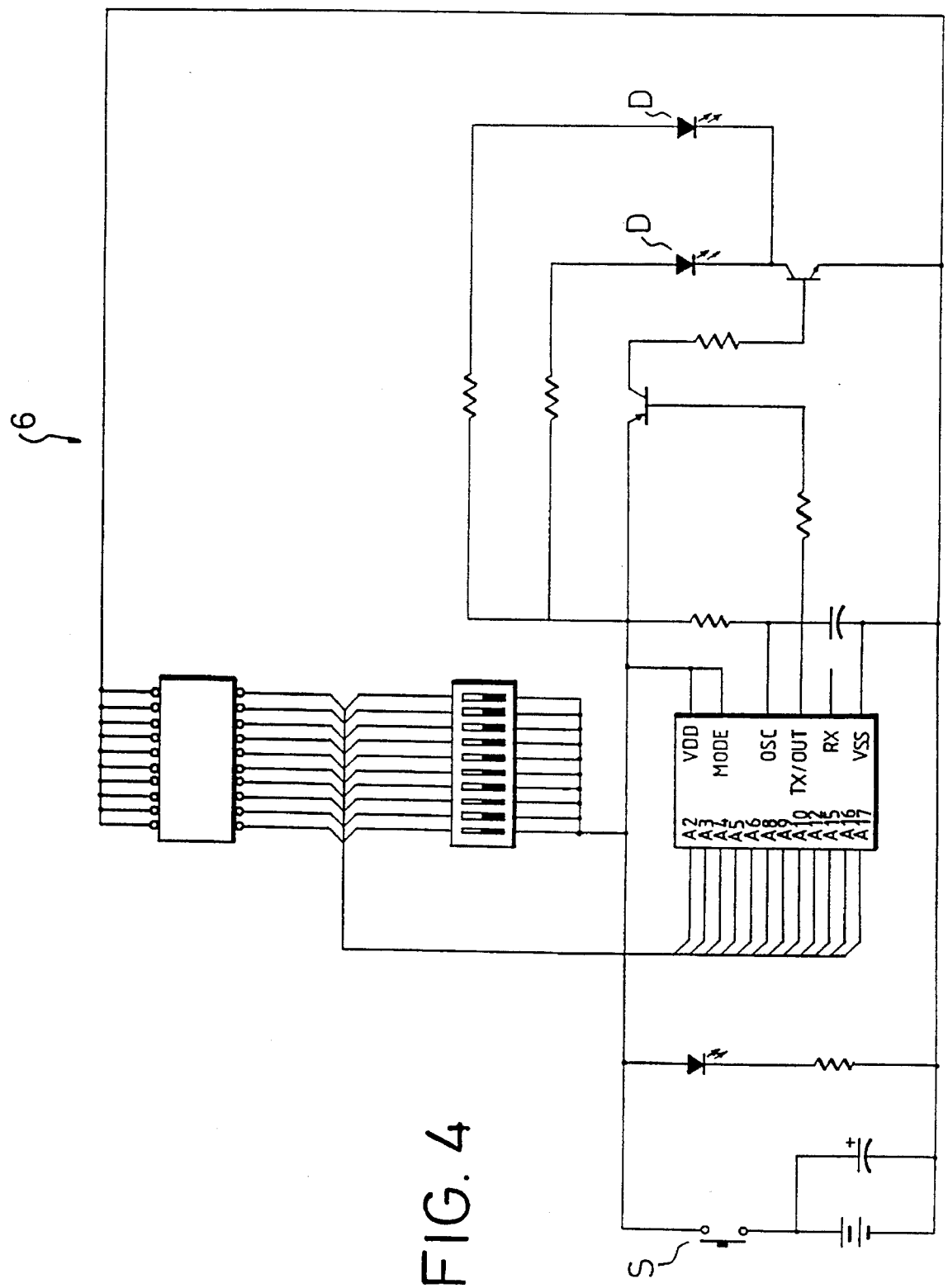
FIG. 4 is a circuit diagram of the transmitter of the present invention.
Figure 5:
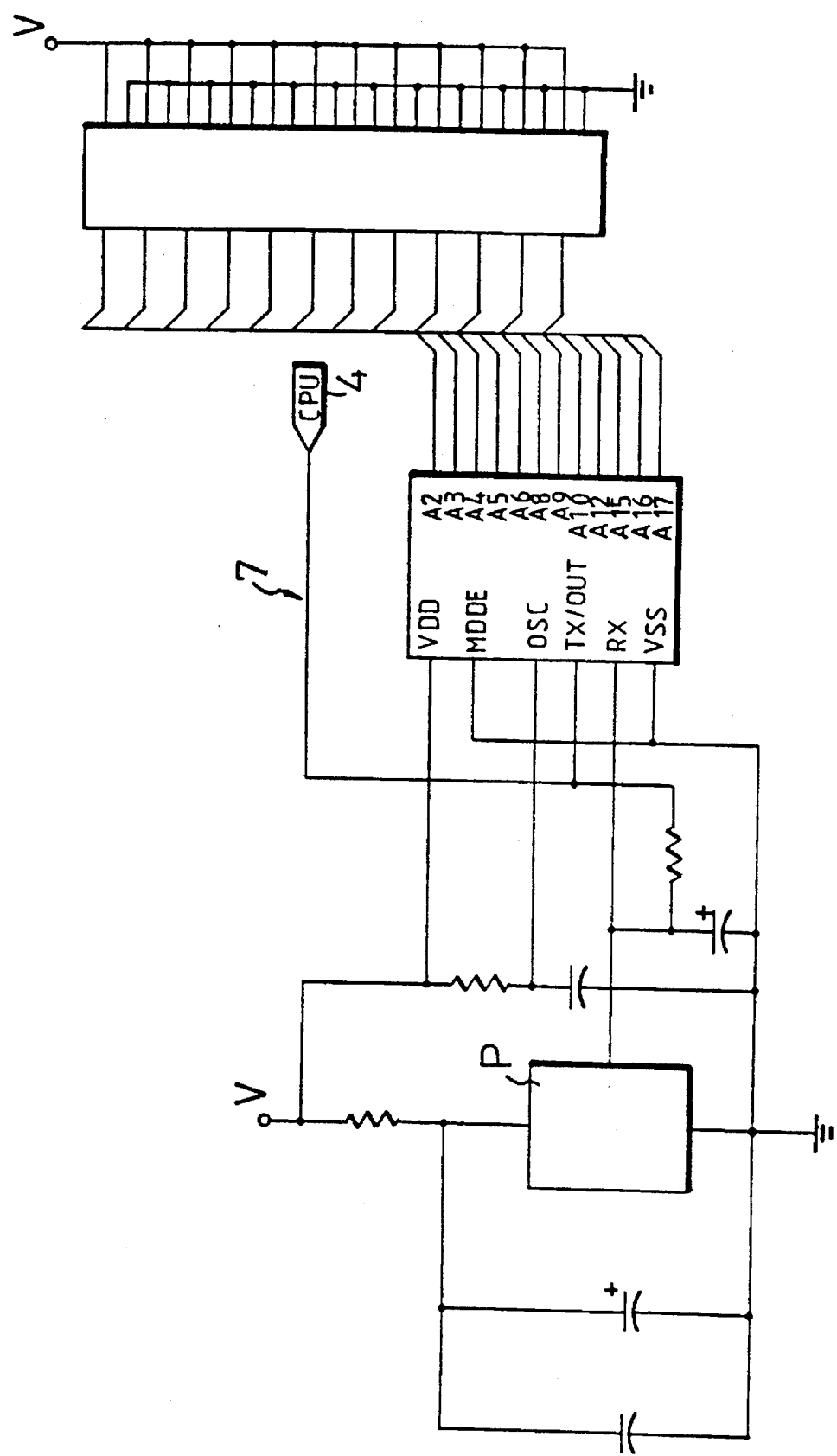
FIG. 5 is a circuit diagram of the receiver of the present invention.

Please refer to FIGS. 4 and 5. At one end of the transmitter 6, a switch S is pressed to make an infrared diode D emit an infrared ray which is received by an infrared sensor P of the receiver 7 so as to output a signal to the amplifying/transferring circuit 8. The signal is processed by the amplifying/transferring circuit 8 and then sent to the microprocessor 4 through a control pin thereof. By means of the input signal of the control pin, the display values of the display circuits 52, 53 are latched, that is, the high and low pressure values are stably displayed by the seven-section displays of the display circuits 52, 53 without variation. The remote transmission of the signals of the transmitter 6 and receiver 7 can be alternatively achieved by means of high frequency wave.

It is to be understood that the above description and drawings are only used for illustrating one embodiment of the present invention, not intended to limit the scope thereof. Any variation and derivation from the above description and drawings should be included in the scope of the present invention.

What is claimed is:

1. In a blood pressure meter, including:

means including a sensor for sensing blood pressure values and generating blood pressure signals representative of the blood pressure values sensed by the sensor;

a display for displaying said blood pressure values; and means including a microprocessor for digitally processing the sensor signals and for generating display control signals to cause said display to display the blood pressure values, said blood pressure values ascending and descending between a low value and a high value, the improvement comprising:

a latch connected between the microprocessor and the display; and means including a receiver connected to the microprocessor and a transmitter having a switch for causing the latch to latch the high and low blood pressure values received from said sensor when a transmitter signal indicative of the switch having been switched is transmitted between the transmitter and the receiver, wherein the display includes first display means made up of an array of light emitting elements for displaying an indication of whether said blood pressure values are increasing or decreasing and second display means for displaying high and low blood pressure values latched by said latch when said transmitter signal is received by said microprocessor.

2. An LED display blood pressure meter as claimed in claim 1, wherein said second display means is made up of two seven segment digital displays.

3. An LED display blood pressure meter as claimed in claim 1, wherein the transmitter transmits an infrared signal.

4. An LED display blood pressure meter as claimed in claim 1, wherein the transmitter transmits a high frequency signal.

* * * * *